United States Patent [19]

Yamamoto et al.

[11] Patent Number: 4,822,823
[45] Date of Patent: Apr. 18, 1989

[54] AQUEOUS PREPARATION AND METHOD OF PREPARATION THEREOF

[75] Inventors: Yujiro Yamamoto, Osaka; Hideo Terayama, Itami; Yasushi Morita, Takasaki, all of Japan

[73] Assignee: Senju Pharmaceutical Co., Ltd., Japan

[21] Appl. No.: 10,534

[22] Filed: Feb. 3, 1987

[30] Foreign Application Priority Data

Feb. 17, 1986 [JP] Japan .................. 61-32265

[51] Int. Cl.$^4$ ............................ A61K 31/12
[52] U.S. Cl. ............................ 514/690
[58] Field of Search ............. 514/778, 58, 688, 678, 514/690

[56] References Cited

FOREIGN PATENT DOCUMENTS 0011475 1/1985 Japan ..................... 514/58

OTHER PUBLICATIONS

"The Merck Index", Tenth Edition, pp. 389 and 390, No. 2712, 1983.
Szejtli, *Journal of Inclusion Phenomena*, vol. 1, pp. 135 to 150, 1983.
*Chem. Abstr.*, 101, No. 8, 307, 60129n, 1984 (corresponds to AT2).
*Chem. Abstr.*, 100, No. 21, 596, 174440s, 1984.
*Patent Abstracts of Japan*, 6, No. 90, May 27, 1982.
*Patent Abstracts of Japan*, 9, No. 228, Sep. 13, 1985.
*Patent Abstracts of Japan*, 5, No. 184, Nov. 21, 1981.
*Patent Abstracts of Japan*, 8, No. 134, Jun. 21, 1984 (corresponds to AR1).

*Primary Examiner*—Douglas W. Robinson
*Attorney, Agent, or Firm*—Berman, Aisenberg & Platt

[57] ABSTRACT

This invention relates to an aqueous preparation comprising a compound (A) represented by the formula:

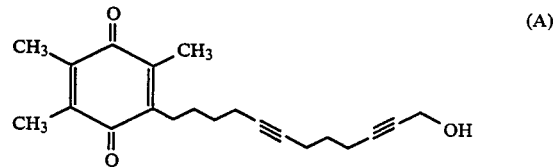

and at least one of cyclodextrins selected from α-cyclodextrin and dimethyl-β-cyclodextrin; and a method of preparation thereof.

According to the aqueous preparation of this invention, coexistence with at least one medicament selected from α-cyclodextrin and dimethyl-β-cyclodextrin allows to enhance the solubility to water of compound (A) essential in this invention to such a concentration that makes an expected curative effect available and to impart a desired stability to it. As a consequence, the aforesaid compound (A) can be utilized as a medicament for an aqueous preparation having anti-allergy action.

9 Claims, No Drawings

AQUEOUS PREPARATION AND METHOD OF PREPARATION THEREOF

BACKGROUND OF THE INVENTION

1. Field of the Invention

This invention relates to an aqueous preparation comprising a compound (A) represented by the formula:

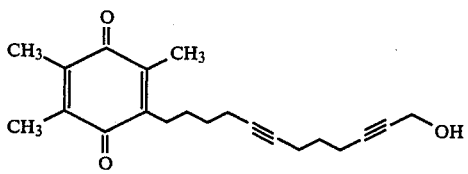

and at least one of cyclodextrins selected from α-cyclodextrin and dimethyl-β-cyclodextrin; and a method of preparation thereof.

2. Description of Prior Art

The aforesaid compound (A) is known to be a selective inhibitor for 5-riboxygenase which is one of important metabolism enzymes for arachidonic acid cascade and to inhibit the production of SRS-A or $LTB_4$, showing experimental allergic asthma which IgG and IgE in Guinea pigs or IgE in rats partake.

In view of the strong anti-allergy action of compound (A), an attempt has been made to develop it as a medicament. However, its solubility is too small to obtain an aqueous solution having a concentration sufficient to exhibit pharmacological effect and consequently, clinical application as an aqueous preparation, such as oral drug, injection drug, nose drops (rhinenchysis drug), eye drops, etc., is expected, but not yet realized in practice.

In local administration of this compound as a liquid preparation, such as a nose drops or eye drops, its concentration is generally required to be from 0.1 to 3 mg/ml.

The compound (A), however, has an extremely low solubility to water, for example, only showing a slight solubility (in the order of less than 10 ng/ml at 25° C.), so that its application as a liquid preparation was regarded as extremely difficult.

SUMMARY OF THE INVENTION

The present inventors have supposed that, if an aqueous preparation which is a clinically applicable form is feasible with use of compound (A), application range of compound (A) will be remarkably enlarged and, consequently, have attempted to make an aqueous preparation containing compound (A).

The present inventors have intensively investigated into the possibility of preparing an aqueous preparation containing compound (A) with a view toward solving the problems above, and as a result, accomplished this invention on the basis of the finding that α-cyclodextrin or dimethyl-β-cyclodextrin remarkably enhances the solubility of compound (A) without impairing its stability.

The present invention consists in an aqueous preparation containing compound (A) and at least one of cyclodextrins selected from α-cyclodextrin and dimethyl-β-cyclodextrin.

According to another aspect, this invention provides a method of preparing an aqueous preparation comprising mixing and dissolving compound (A) and a cyclodextrin in an aqueous solvent.

The aqueous preparation of this invention can be advantageously used for medicinal utility, for example, in the form of a nose drops, eye drops, embrocation, inhalant, oral drug, injection drug, etc.

As a medicament to be compounded in order to raise the solubility of compound (A) to water, at least one cyclodextrin (selected from α-cyclodextrin and dimethyl-β-cyclodextrin) is used.

An aqueous preparation is obtained by dissolving the aforesaid compound (A) and the aforesaid cyclodextrin in water, with compound (A) being contained in an amount of 0.001 to 0.5 w/v %, preferably 0.01 to 0.3 w/v % based on the totality of the aqueous preparation.

Our experimental investigation has revealed that α-cyclodextrin shows a highly advantageous effect for the intended object whereas β-cyclodextrin and γ-cyclodextrin do not show any intended effect and that dimethyl-β-cyclodextrin shows a similar effect to α-cyclodextrin.

The amount of α-cyclodextrin and/or dimethyl-β-cyclodextrin to be incorporated in an aqueous preparation of this invention is desired to be usually 0.1 to 15 w/v %, preferably, 1~10 w/v %.

In the aqueous preparation of this invention, there may be incorporated conventional additives which are usually used for an aqueous preparation, for example, a buffer for pH adjustment (phosphoric acid buffer, boric acid buffer, citric acid buffer, tartaric acid buffer, acetic acid buffer, etc.); isotonic-rendering agent (sorbitol, glycerine, polyethylene glycol, propylene glycol, glucose, sodium chloride, etc.); antiseptic (benzalkonium chloride, paraoxybenzoic esters, benzyl alcohol, para-chlorometaxylenol, chlorocresol, phenethyl alcohol, sorbic acid or its salts, thimerosal, chlorobutanol, etc.); chelating agent (sodium edetate, sodium citrate, sodium polyphosphate, etc.); thickener (polyvinyl pyrrolidone, methyl cellulose, sodium carboxymethyl cellulose, hydroxyethyl cellulose, hydroxypropyl cellulose, polyvinyl alcohol, sodium polyacrylate, etc.) in a usual amount.

Any medicinal ingredient other than compound (A) may also be incorporated in the aqueous preparation of this invention insofar as the intended object of this invention is not impaired.

The pH of the aqueous preparation of this invention is usually within the range of 3 to 10, preferably 4 to 8.

The aqueous preparation of this invention is usually prepared by incorporating and dissolving compound (A) and a cyclodextrin in an aqueous solvent. Particularly, it is preferred, after dissolution, to subject the resulting solution to pH adjustment and further to sterilization treatment.

In preparing nose drops, eye drops, etc., it is desirable that, after an antiseptic is dissolved in an aqueous solvent, a cyclodextrin is incorporated, and compound (A) is incorporated, if necessary, together with a buffer, isotonic-rendering agent, chelating agent, thickener, etc., to completely dissolve it.

The sterilization treatment includes, for example, heat treatment, filtration and the like.

In compounding a medicinal ingredient other than compound (A), such may be added at any stage insofar as the object of this invention is not deviated, but desirably, it is added after compound (A) is dissolved.

The invention will be hereinbelow described in more detail with reference to experimental examples and working examples.

EXPERIMENTAL EXAMPLE 1

Examination of Solubility

In order to demonstrate the effect of increase in solubility of compound (A) when α-cyclodextrin or dimethyl-β-cyclodextrin is compounded with it, comparative solubility test was effected between α-cyclodextrin or dimethyl-β-cyclodextrin and various kinds of dissolution-assisting agents as a control. The dissolution-assisting agents used as a control are β-cyclodextrin, γ-cyclodextrin, polyvinyl pyrrolidone (hereinbelow abbreviated as PVP), polyoxyethylene monostearate (hereinbelow abbreviated as MYS-40), polyoxyethylene sorbitan monooleate (hereinbelow abbreviated as TO-80), and polyoxyethylene cured castor oil (hereinbelow abbreviated as HCO-40, HCO-60). As a result, prominent enhancement of solubility was observed with α-cyclodextrin and dimethyl-β-cyclodextrin whereas such effect was hardly observed with the control dissolution-assisting agents.

Solubility was determined by dissolving the respective dissolution-assisting agents into 0.2 mole of phosphoric acid buffer solution ($Na_2HPO_4NaH_2PO_4$, pH 6.0), then adding excessive amount of compound (A) and shaking the mixed solution at room temperature (15° C.~20° C.) for 5 days, centrifuging the solution, filtering the supernatant by use of cotton stoppers, and subsequently measuring the concentration of compound (A) contained in the filtrate with a high-speed liquid chromatography.

Results are shown in Table 1.

TABLE 1

| Dissolution-Assisting Agent | Addition Amount (w/v %) | Solubility of Compound (A) (w/v %) |
|---|---|---|
| α-CD | 1.0 | 0.0358 |
|  | 2.0 | 0.0825 |
|  | 5.0 | 0.1770 |
| Dimethyl-β-CD | 1.0 | 0.0461 |
|  | 2.0 | 0.0933 |
|  | 5.0 | 0.1825 |
| β-CD | 0.2 | 0.0013 |
|  | 0.4 | 0.0025 |
|  | 1.25 | 0.0039 |
| γ-CD | 0.4 | 0.0004 |
|  | 0.8 | 0.0003 |
|  | 2.0 | 0.0001 |
| PVP(K-30) | 0.1 | 0.0005 |
|  | 0.2 | 0.0006 |
|  | 0.5 | 0.0005 |
| MYS-40 | 0.1 | 0.0057 |
|  | 0.2 | 0.0101 |
|  | 0.5 | 0.0172 |
| TO-80 | 0.1 | 0.0081 |
|  | 0.2 | 0.0128 |
|  | 5.0 | 0.0219 |
| HCC-40 | 0.1 | 0.0098 |
|  | 0.2 | 0.0149 |
|  | 5.0 | 0.0213 |
| HCO-60 | 0.1 | 0.0062 |
|  | 0.2 | 0.0132 |
|  | 5.0 | 0.0191 |
| Phosphoric acid buffer solution | — | 0.0002 |

Note:
"CD" denotes cyclodextrin.

As will be apparent from these results, it was unexpected that α-cyclodextrin and dimethyl-β-cyclodextrin exhibit a conspicuous solubility-enhancing effect of 1000 times as high as that of phosphoric acid buffer having pH 6 whereas β-cyclodextrin or γ-cyclodextrin can hardly enhance the solubility. The other dissolution-assisting agents showed little increase in solubility to the degree that is practically available, either.

EXPERIMENTAL EXAMPLE 2

Stability test of compound (A) was performed in the following formula at varying pHs:

Formula

| | |
|---|---|
| Compound (A) | 0.05 g |
| α-Cyclodextrin | 5.0 g |
| $Na_2HPO_4.H_2O$ | 0.5 g |
| $H_3PO_4$ | proper amount |
| Purified Water | amount totaling 1000 ml |

Results are shown in Table 2.

TABLE 2

| Preservation Conditions | pH | | | |
|---|---|---|---|---|
|  | 4.0 | 5.0 | 6.0 | 7.0 |
| 60° C.-3 days | 101.2% | 102.6% | 102.5% | 93.3% |
| 60° C.-5 days | 102.5% | 99.5% | 102.8% | 87.6% |
| Room temp.-5 days | 99.6% | 103.0% | 99.4% | 99.1% |

Note: The data are represented in terms of persistence rate (%).

As a result, it has become apparent that the aqueous preparation of this invention is stable in the pH range of 4 to 6.

Further stability test at 60° C. with a high-speed liquid chromatography was effected in accordance with the formulae given below containing, as a dissolution-assisting agent, TO-80 and α-cyclodextrin, respectively.

| | Formula 1 | Formula 2 |
|---|---|---|
| Compound (A) | 0.01 g | 0.01 g |
| α-CD | 3.0 g | — |
| TP-80 | — | 0.3 g |
| Sodium Acetate | 0.1 g | 0.1 g |
| Acetic Acid | proper amount | proper amount |
|  | pH 5 | pH 5 |
| Purified Water | totaling 1000 ml | totaling 1000 ml |

Results obtained are given in Table 3.

TABLE 3

| | 1 Week | 2 Weeks | 3 Weeks |
|---|---|---|---|
| Formula 1 | 97.9 | 98.9 | 91.5 |
| Formula 2 | 89.1 | 78.2 | 68.1 |

Note:
The data are represented in terms of persistence rate (%).

It was proved that the formula containing α-cyclodextrin is more stable than the formula containing TO-80.

PHARMACEUTICAL EXAMPLE 1 (Nose drops)

| | |
|---|---|
| Compound (A) | 5 g |
| Disodium phosphate | 1.4 g |
| Monosodium phosphate | 2.6 g |
| α-Cyclodextrin | 100 g |
| Concentrated glycerine | 15 g |
| Sodium hydroxide | proper amount |
| Methyl p-oxybenzoate | 2.0 g |
| Propyl p-oxybenzoate | 0.5 g |
| Benzyl alcohol | 3.0 g |

| -continued | |
|---|---|
| Purified water | totaling 1.0 l |

In 800 ml of purified water being heated, methyl p-oxybenzoate and propyl p-oxybenzoate were dissolved, and disodium phosphate, monosodium phosphate, α-cyclodextrin and concentrated glycerine were added in sequence and heated, and then, compound (A) was dissolved. After cooling, benzyl alcohol was added and dissolved, and the solution obtained was adjusted to pH 6.0 with sodium hydroxide and totaled to 1.0 l by the addition of purified water. The solution was filtered through a 0.45μ membrane filter, and filled in a predetermined container to produce a liquid preparation for nose drops.

PHARMACEUTICAL EXAMPLE 2 (Eye drops)

| Compound (A) | 1 g |
|---|---|
| Sodium Acetate | 2 g |
| Acetic Acid | proper amount |
| Dimethyl-β-cyclodextrin | 30 g |
| Sodium chloride | 7.5 g |
| Polyethylene glycol | 5 g |
| Propyl paraoxybenzoate | 0.14 g |
| Benzalkonium chloride | 0.05 g |
| Sterilized, purified water | added to total 1.0 l |

Sterilized, purified water, 800 ml, was heated, propyl p-oxybenzoate was dissolved, and then, sodium acetate, dimethyl-β-cyclodextrin, polyethylene glycol, sodium chloride and compound (A) were added in sequence and dissolved. After cooling, sodium chloride was dissolved, the solution obtained was adjusted to pH 5 with acetic acid, and finally, sterilized, purified water was added to make 1.0 l. The solution was filtered through a 0.22μ membrane filter, and filled in a predetermined container to make a liquid preparation for eye drops.

According to the aqueous preparation of this invention, coexistence with at least one medicament selected from α-cyclodextrin and dimethyl-β-cyclodextrin allows to enhance the solubility to water of compound (A) essential in this invention to such a concentration that makes an expected curative effect available and to impart a desired stability to it. As a consequence, the aforesaid compound (A) can be utilized as a medicament for an aqueous preparation having anti-allergy action.

What is claimed is:

1. An aqueous preparation comprising the compound (A) represented by the formula:

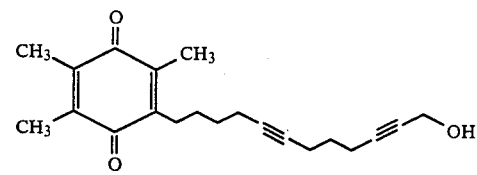

and at least one cyclodextrin selected from the group consisting of α-cyclodextrin and dimethyl-β-cyclodextrin wherein the content of compound (A) is in the range of from 0.001 to 0.5 w/v %, and the cyclodextrin content is in the range of from 0.1 to 15 w/v % and wherein the pH is 3-10.

2. An aqueous preparation as claimed in claim 1, wherein the content of compound (A) is in the range of from 0.001 to 0.01 w/v %, and the cyclodextrin content is in the range of from 0.1 to 15 w/v %.

3. An aqueous preparation as claimed in claim 1 or 2, whose pH is 4-8.

4. An aqueous preparation as claimed in claim 1 or 2, which is in the form of eye drops, injection drug, or nose drops.

5. A method of significantly increasing solubility of compound (A)

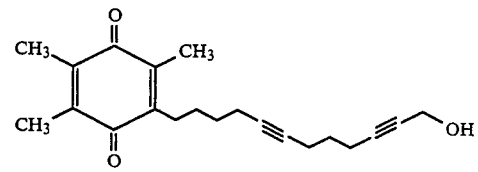

in an aqueous medium which comprises incorporating in such medium a sufficient amount of a cyclodextrin selected from the group consisting of α-cyclodextrin and dimethyl-β-cyclodextrin.

6. A method as claimed in claim 5 which comprises, after dissolution, adjusting the pH of the aqueous medium to 3~10.

7. A method as claimed in claim 6, which comprises, after pH adjustment, effecting sterilization treatment.

8. A method as claimed in claim 6 or 7, wherein the content of compound (A) is from 0.001 to 0.5 w/v % and the cyclodextrin content is from 0.1 to 15 w/v %.

9. An aqueous preparation as claimed in claim 3, which is in the form of eye drops, an injection drug or nose drops.

* * * * *